US012183216B1

(12) United States Patent
Lyu et al.

(10) Patent No.: US 12,183,216 B1
(45) Date of Patent: Dec. 31, 2024

(54) LANDSLIDE MODEL TEST DEVICES AND METHODS FOR REALIZING MULTI-VARIABLE SYNCHRONOUS MONITORING

(71) Applicant: ZHEJIANG UNIVERSITY, Zhejiang (CN)

(72) Inventors: Qing Lyu, Hangzhou (CN); Peng Liu, Hangzhou (CN); Xinghua Xu, Hangzhou (CN); Junyu Wu, Hangzhou (CN); Xinfa Gong, Hangzhou (CN); Zihao Deng, Hangzhou (CN); Liming Zhang, Hangzhou (CN); Zhenghua Liu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 18/765,185

(22) Filed: Jul. 5, 2024

(30) Foreign Application Priority Data

Jul. 5, 2023 (CN) .......................... 202310817679.2

(51) Int. Cl.
   *G09B 23/40* (2006.01)
   *G01N 33/24* (2006.01)

(52) U.S. Cl.
   CPC ........... *G09B 23/40* (2013.01); *G01N 33/246* (2013.01)

(58) Field of Classification Search
   CPC .............................. G09B 23/40; G01N 33/246
   See application file for complete search history.

(56) References Cited

U.S. PATENT DOCUMENTS

| 2016/0115517 A1 | 4/2016 | Heijstra et al. |
| 2019/0113496 A1* | 4/2019 | Tang ..................... G01N 33/246 |
| 2024/0105083 A1* | 3/2024 | Lan ......................... G09B 25/04 |

FOREIGN PATENT DOCUMENTS

| CN | 102174816 A | 9/2011 |
| CN | 109100300 A | 12/2018 |
| CN | 110793964 A | 2/2020 |
| CN | 110967468 A | 4/2020 |

(Continued)

OTHER PUBLICATIONS

CN-113156083-A (Year: 2021).*

(Continued)

*Primary Examiner* — Kristina M Deherrera
*Assistant Examiner* — Fatemeh Esfandiari Nia
(74) *Attorney, Agent, or Firm* — Porus IP LLC

(57) ABSTRACT

The present disclosure relates to the technical field of landslide hazard model tests, and in particular to a landslide model test method and device for realizing multi-variable synchronous monitoring. In the test device, a soil slope simulation unit is configured to pile up a soil slope and simulate different inclinations of the slope. A rainfall simulation unit is configured to simulate rainfall of different intensities and induce a landslide. A runoff-seepage separation unit is configured to realize separation of runoff from seepage of the slope under the effect of rainfall. A monitoring module is configured to monitor runoff and seepage flow rates of the slope, changes in water content and pore water pressure within the slope, and a morphological change of the slope under the effect of rainfall, to obtain a mechanism of rainfall-induced landslide deformation and damage based on changes in the flow rate.

8 Claims, 4 Drawing Sheets

(56) References Cited

FOREIGN PATENT DOCUMENTS

| CN | 113156083 | A | * | 7/2021 | ............. G01N 33/24 |
| --- | --- | --- | --- | --- | --- |
| CN | 113376073 | A | | 9/2021 | |
| CN | 113418831 | A | * | 9/2021 | |
| CN | 214613956 | U | | 11/2021 | |
| CN | 115792180 | A | * | 3/2023 | |

OTHER PUBLICATIONS

CN-113418831-A (Year: 2021).*
CN-115792180-A (Year: 2023).*
CN109100300A (Year: 2018).*
First Office Action in Chinese Application No. 202310817679.2 mailed on Apr. 25, 2024, 17 pages.
Notification to Grant Patent Right for Invention in Chinese Application No. 202310817679.2 mailed on May 10, 2024, 4 pages.
Yang, Hongwel, Simulation of seepage flow in unsaturated soil under different rainfall intensity, Geotechnical Investigation & Surveying, 2019, 8 pages.
Liu, Peng et al., Mechanism Analysis of Landslide Hazards Induced by Rainwater Infiltration, Soil eng. & foundation, 24(3): 33-35, 2010.
Yu, Yuanxiang et al.. Analysis on Deformation Mechanism of Loess Landslide in Thongchuan Area, China Mining Magizine, 15(12): 70-72, 2006.

* cited by examiner

LANDSLIDE MODEL TEST DEVICES AND METHODS FOR REALIZING MULTI-VARIABLE SYNCHRONOUS MONITORING

CROSS REFERENCE TO RELATED APPLICATIONS

This application claims priority to Chinese Patent Application No. 202310817679.2, filed on Jul. 5, 2023, the entire contents of which are incorporated herein by reference.

TECHNICAL FIELD

The present disclosure relates to the technical field of landslide hazard model testing, and in particular to a landslide model test method and device for realizing multi-variable synchronous monitoring.

BACKGROUND

Landslide refers to the natural phenomenon that the rock and soil on the slope slides down the slope as a whole or in a scattered manner along a certain weak surface or weak zone under the action of gravity due to factors such as river scouring, groundwater activity, rainwater soaking, earthquakes, and artificial slope cutting. A rainfall-induced landslide is the most common type of geological hazard, which often causes huge casualties and economic losses.

When rainwater acts on the slope, part of the rainwater flows away in the form of surface runoff, and the other part of the rainwater enters the soil and produce underground seepage. Accurately monitoring the flow rate of slope surface runoff and slope seepage under different rainfall conditions and the changes in soil water content and pore water pressure within the slope is of great value in understanding the hydrological response mechanism of the slope under rainfall and the impact on slope stability. The indoor model test of a landslide is an effective means to study the mechanism of deformation and damage of the rainfall-induced landslide, and is of great significance for the prevention and mitigation of the rainfall-induced landslide.

However, since a runoff and seepage flow rate of an indoor model slope is small and mixed with soil, rocks, etc., conventional means of water flow monitoring are not applicable. The flow monitoring of the existing landslide model test mainly relies on manual work, which is long in monitoring time interval and difficult to accurately capture the detailed changes in the hydrological response of the slope before and after the landslide occurs. In addition, the flow monitoring in the prior art mostly focuses on a mixture of runoff and seepage, and does not distinguish between the dynamic changes of rainwater runoff on the slope surface and seepage flow within the slope. The rainfall-induced landslide is often accompanied by changes in runoff and seepage flow rates before the rainfall-induced landslide occurs. To this end, it is necessary to monitor the runoff and seepage flow rates separately in combination with the change data and image data of the water content and the pore water pressure within the slope to provide data reference for the research and analysis of the initiation mechanism of the rainfall-induced landslide.

SUMMARY

One of the embodiments of the present disclosure provide a landslide model test device for realizing multi-variable synchronous monitoring, comprising: a soil slope simulation unit, configured to pile up a soil slope and simulate different inclinations of the slope, the soil slope simulation unit including a model slot; a rainfall simulation unit, cooperated with the soil slope simulation unit and configured to simulate rainfall of different intensities and induce a landslide; a runoff-seepage separation unit, disposed at an end of the soil slope simulation unit and configured to implement separation of runoff from seepage of the slope under the effect of rainfall; the runoff-seepage separation unit including a porous plate disposed at an end of the model slot, wherein a runoff water chute may be disposed at a position behind the porous plate corresponding a slope surface of the soil slope, and a seepage water chute may be disposed at a position behind the porous plate corresponding a bedrock surface of the soil slope; and a monitoring module, cooperated with the runoff-seepage separation unit and configured to monitor runoff and seepage flow rates of the slope, changes in water content and pore water pressure within the slope, and a morphological change of the slope under the effect of rainfall; wherein the monitoring module may include a flow rate monitoring unit, disposed at an end of the runoff-seepage separation unit and configured to monitor the runoff and seepage flow rates of the slope under the effect of rainfall; the flow rate monitoring unit may include two sedimentation tanks connected with the runoff water chute and the seepage water chute, respectively, each of the two sedimentation tanks may be connected with a water collection tank through a second guide pipe; the second guide pipe may be disposed at an upper edge of the corresponding sedimentation tank; a horizontal height of the water collection tank may be lower than a horizontal height of the corresponding sedimentation tank; and a weighing device may be provided under each of the two sedimentation tanks and the water collection tank.

In some embodiments, the soil slope may be disposed in the model slot. A hoisting mechanism may be disposed at a front end of the model slot in a cooperated manner. A bottom of a rear end of the model slot may be hinged on a hinge support. The hinge support may be placed on a horizontal plane.

In some embodiments, the hoisting mechanism may include a bracket disposed on the horizontal plane. A chain hoist may be disposed at an upper portion of the bracket. The chain hoist may be cooperated with a hanging ring disposed at the front end of the model slot through a hoisting ring.

In some embodiments, the rainfall simulation unit may include one or more spray nozzles cooperated with an upper portion of the model slot. The one or more spray nozzles may be connected with a water supply end through a water inlet pipe.

In some embodiments, the runoff water chute and the seepage water chute may be cooperated with the monitoring module through a first guide pipe.

In some embodiments, the monitoring module may further include: a plurality of sensors, disposed within the soil slope and configured to monitor the changes in the water content and the pore water pressure within the soil slope under effect of rainfall; and one or more cameras, disposed at a side of the soil slope simulation unit and configured to record the morphological change of the soil slope.

In some embodiments, the plurality of sensors may include a plurality of pore water pressure sensors and a plurality of water content sensors configured to collect changes in parameters within the soil slope under the effect of rainfall. The plurality of pore water pressure sensors and the plurality of water content sensors may be buried at different depths within the soil slope in a direction perpendicular to the bedrock surface.

One or more embodiments of the present disclosure provide a landslide model test method, implemented by a landslide model test device for realizing multi-variable synchronous monitoring, comprising: piling up a soil slope and simulating different inclinations of the slope by a soil slope simulation unit, simulating rainfall of different intensities and inducing a landslide by a rainfall simulation unit, implementing separation of runoff from seepage at the soil slope simulation unit by a runoff-seepage separation unit during simulation of rainfall of different intensities, and monitoring runoff and seepage flow rates of the slope, changes in water content and pore water pressure within the slope, and a morphological change of the slope under the effect of rainfall by a monitoring module, to obtain a mechanism of rainfall-induced landslide deformation and damage based on synergistic analysis of multi-variable data.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering indicates the same structure, wherein.

Figure 1:
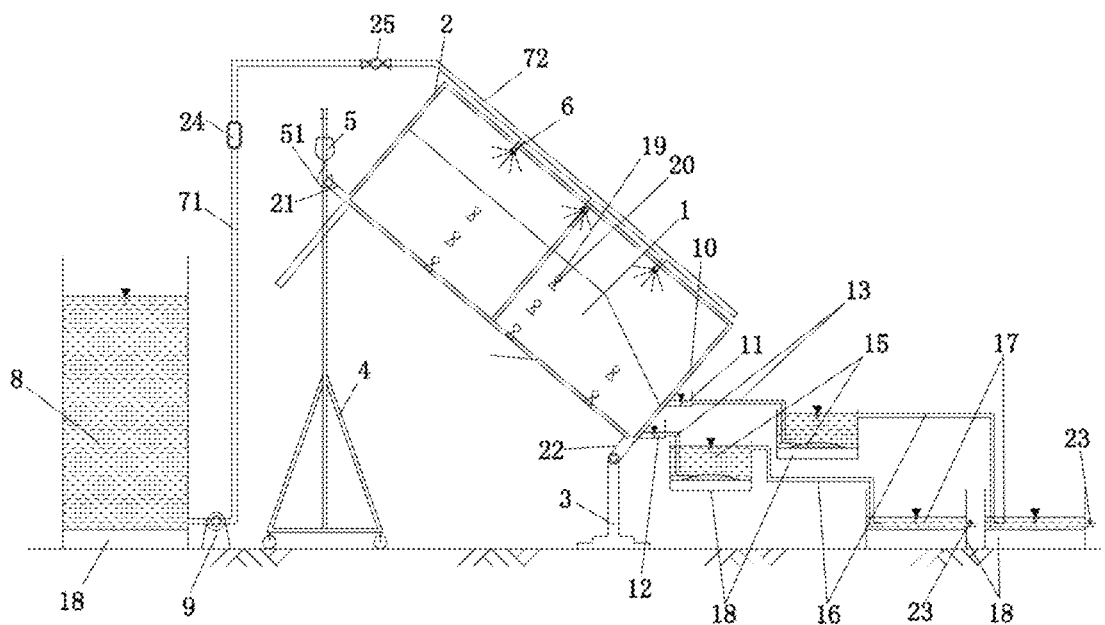
FIG. 1 is a schematic structural diagram illustrating an exemplary landslide model test device according to some embodiments of the present disclosure.

Reference signs in the figure: 1—soil slope; 2—model slot; 3—hinge support; 4—bracket; 5—chain hoist; 51—hoisting ring; 6—spray nozzle; 8—water supply end; 9—water pump; 10—porous plate; 11—runoff water chute; 12—seepage water chute; 13—first guide pipe; 14—camera; 15—sedimentation tank; 16—second guide pipe; 17—water collection tank; 18—weighing device; 19—pore water pressure sensor; 20—water content sensor; 21—hanging ring; 22—support leg; 23—drainage valve; 24—first temperature control subunit; 25—precipitation regulation valve; 31—support unit; 71—rigid pipe; 72—flexible pipe.

DETAILED DESCRIPTION

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for a person having ordinary skills in the art to apply the present disclosure to other similar scenarios in accordance with these drawings without creative labor. Unless obviously obtained from the context or the context illustrates otherwise, the same numeral in the drawings refers to the same structure or operation.

It should be understood that "system", "device", "unit" and/or "module" as used herein is a method for distinguishing different components, elements, parts, portions or assemblies of different levels. However, the words may be replaced by other expressions if other words can achieve the same purpose.

As indicated in the disclosure and claims, the terms "a", "an", and/or "the" are not specific to the singular form and may include the plural form unless the context clearly indicates an exception. Generally speaking, the terms "comprising" and "including" only suggest the inclusion of clearly identified steps and elements, and these steps and elements do not constitute an exclusive list, and the method or device may also contain other steps or elements.

In order to solve the problem that flow monitoring of a landslide model test mainly relies on manual work, and is long in monitoring time interval and difficult to accurately capture detailed changes in the hydrological response of a slope before and after the landslide occurs, the present disclosure provides a landslide model test method and device for realizing multi-variable synchronous monitoring, which can realize automatic and real-time monitoring of runoff and seepage flow rates of the slope, and can also monitor changes in water content and pore water pressure within the slope and a morphological change of the slope.

Referring to FIG. 1, FIG. 1 is a schematic structural diagram illustrating an exemplary landslide model test device according to some embodiments of the present disclosure. The landslide model test device may include a soil slope simulation unit, a rainfall simulation unit, a runoff-seepage separation unit, and a monitoring module.

The soil slope simulation unit may be configured to pile up a model of a soil slope 1 and simulate different inclinations of the slope. The soil slope simulation unit may include a model slot 2. The soil slope 1 may be disposed in the model slot 2.

The rainfall simulation unit may be cooperated with the soil slope simulation unit and configured to simulate rainfall of different intensities and induce a landslide.

The runoff-seepage separation unit may be disposed at an end of the soil slope simulation unit and configured to implement separation of runoff from seepage of the slope under the effect of rainfall. The runoff-seepage separation unit may include a porous plate 10 disposed at an end of the model slot 2. A runoff water chute 11 may be disposed at a position behind the porous plate 10 corresponding a slope surface of the soil slope 1. A seepage water chute 12 may be disposed at a position behind the porous plate 10 corresponding a bedrock surface of the soil slope 1.

The monitoring module may be cooperated with the runoff-seepage separation unit and configured to monitor runoff and seepage flow rates of the slope, changes in water content and pore water pressure within the slope, and a morphological change of the slope under the effect of rainfall.

In some embodiments, the monitoring module may include a flow rate monitoring unit disposed at an end of the runoff-seepage separation unit and configured to monitor the runoff and seepage flow rates of the slope under the effect of rainfall.

In some embodiments, the flow rate monitoring unit may include two sedimentation tanks 15 connected with the runoff water chute 11 and the seepage water chute 12, respectively. Each of the two sedimentation tanks 15 may be connected with a water collection tank 17 through a second guide pipe 16. The second guide pipe 16 may be disposed at an upper edge of the corresponding sedimentation tank 15. A horizontal height of the water collection tank 17 may be lower than a horizontal height of the corresponding sedimentation tank 15. A weighing device 18 may be provided under each of the two sedimentation tanks 15 and the water collection tank 17.

In some embodiments, the soil slope simulation unit may realize simulation of different inclinations of the soil slope. When the rainfall simulation unit realizes simulation of rainfall, simulated "rainwater" (water flow) may flow down along the slope surface of the soil slope 1 or seep into the soil slope 1. The runoff and seepage separation unit may implement separation of runoff and seepage. The monitoring module may monitor flow rates of runoff and seepage. In the present disclosure, a water flow direction may be defined as positive and a start position may be defined as "front".

Figure 4:
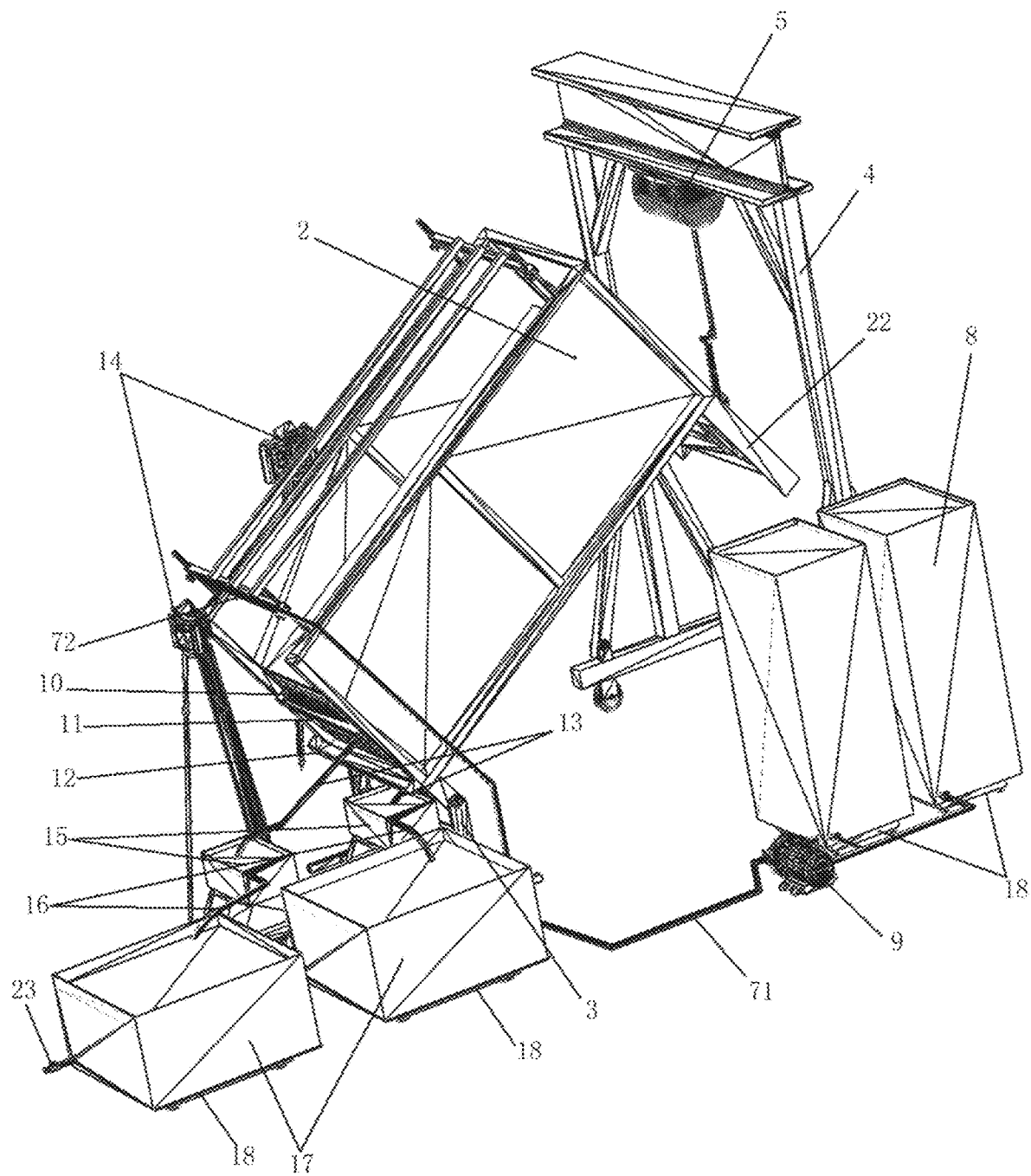
FIG. 4 is a schematic structural diagram illustrating an exemplary landslide model test device after assembly according to some embodiments of the present disclosure.

Meanwhile, referring to FIG. 4, FIG. 4 is a schematic structural diagram illustrating an exemplary landslide model test device after assembly according to some embodiments of the present disclosure. In some embodiments, a soil slope simulation unit may include the model slot 2. The soil slope 1 may be disposed in the model slot. A hoisting mechanism may be disposed at a front end of the model slot 2. A bottom of a rear end of the model slot 2 may be hinged on the hinge support 3. The hinge support 3 may be placed on a horizontal plane.

In some embodiments, the hoisting mechanism may include a bracket 4 disposed on the horizontal plane. A chain hoist 5 may be disposed at an upper portion of the bracket. The chain hoist 5 may be cooperated with a hanging ring 21 disposed at the front end of the model slot 2 through a hoisting ring 51.

In some embodiments, the model slot 2 may include a bottom plate. A front side plate, a left side plate, and a right side plate may be disposed on the bottom plate (without rear side plate). In order to facilitate rainfall simulation of the rainfall simulation unit, four support legs 22 may be disposed under the bottom plate. The support legs 22 disposed at a rear end of the model slot 2 may be hinged to a top of the hinge support 3, so that the bottom plate of the model slot 2 may have a certain height from the ground. In addition, the bracket 4 of the hoisting mechanism may be disposed at the front end of the model slot 2. The bracket 4 may be a gantry, and the gantry may lift the hoisting ring 21 through the chain hoist 5, so that the front end of the model slot 2 may achieve a height change, thereby adjusting an inclination angle of the model slot 2, i.e., an inclination angle of the soil slope 1.

In some embodiments, a main structure of the model slot 2 may be a cuboid steel frame formed by welding 12 steel pipes, with steel as the bottom plate at a bottom end. The slope of the piled soil slope may change along a long side of the frame. The left and right sides may be generally connected to an inner side of the steel frame with tempered glass, and the front side plate may be welded to the frame as a whole with a steel plate to ensure the overall strength and rigidity.

In some embodiments, the rainfall simulation unit may include a plurality of spray nozzles 6 disposed at an upper portion of the model slot 2 in a cooperated manner. All the spray nozzles 6 may be connected to a water supply end 8 through a water inlet pipe.

In some embodiments, the water supply end 8 may include but is not limited to a water tank and/or municipal water. A flow rate measurement mechanism or an electronic weighing device may be cooperated with the water supply end 8. In some embodiments, the electronic weighing device (e.g., weighing device 18) may be provided under the water tank to monitor a mass change of the water tank in real time and obtain a real-time rainfall intensity.

In some embodiments, in order to facilitate the connection between the plurality of spray nozzles 6 and the water supply end 8, the water inlet pipe may include a rigid pipe 71 and flexible pipes 72 which are connected. A water pump 9 may be disposed between the rigid pipe 71 and the water supply end 8. The four flexible pipes 72 may be independent of each other and connected with the rigid pipe 71 through a one-to-four water valve. The four flexible pipes 72 may be provided with 2, 4, 8, and 8 spray nozzles 6, respectively. When water is introduced into the flexible pipes 72, a water spray rate of a single spray nozzle 6 may remain constant. Through on-off combinations of whether the water is introduced into the four flexible pipes 72, 11 situations in total, namely, 2, 4, 6, 8, 10, 12, 14, 16, 18, 20, and 22 spray nozzles 6 corresponding to 11 rainfall intensities may be realized.

In some embodiments, the plurality of spray nozzles 6 connected to each flexible pipe 72 may be evenly disposed above the slope to ensure that the slope receives even rainfall under the 11 rainfall intensities.

Since temperature fluctuations cause soil to expand or contract, especially during a freeze-thaw cycle, changes in soil volume may affect the structural integrity. In addition, temperature changes also affect the evaporation and condensation of water in the soil, thereby affecting the moisture and strength of the soil. Therefore, in some embodiments, the control of ambient temperature and wind force may also be added during the landslide model test.

In some embodiments, the rainfall simulation unit may include a first temperature control subunit 24, a second temperature control subunit, and a wind control subunit. In some embodiments, the first temperature control subunit 24 may be disposed on the rigid pipe 71 and configured to control water flow temperature of a water flow in the rigid pipe 71. The second temperature control subunit may be disposed in the model slot 2 and configured to control an ambient temperature in the model slot 2. The wind control subunit may be disposed in the model slot 2 and configured to control gas parameters in the model slot 2.

In some embodiments, the first temperature control subunit 24 may include a heater or a refrigerator, etc. The second temperature control subunit may include a temperature distribution control device, such as a fan or a ventilation system, on the basis of the heater or the refrigerator to help the second temperature control subunit form a uniform temperature field in the model slot 2.

In some embodiments, the wind control subunit may include fan blades and wind speed and air volume controllers to adjust wind speed and an air flow entering the model slot 2 according to test requirements.

In some embodiments, the landslide model test device may further include a processor (e.g., a CPU or an MCU, etc.). The processor may be configured to determine test parameters based on soil slope structure data of the soil slope 1; and send the test parameters to a user.

The test parameters may include a rainfall amount, a rainfall pattern, a rainfall intensity, and the ambient temperature. Selecting appropriate test parameters may better collect test data and avoid waste of resources or data redundancy caused by the soil slope being washed away too quickly or the rainfall having little impact on the soil slope. The rainfall pattern may be used to simulate different rainfall conditions, such as gradually increasing or decreasing rainfall.

The soil slope structure data may include slope soil quality data, a slope inclination, soil layer thickness, soil sparseness, etc. The slope soil quality data may include a soil type (e.g., clay, sand, loam, etc.) of the slope. Soil properties may include permeability, particle composition (including particle size), density, etc. The soil slope structure data may be determined according to an actual situation before the test.

In some embodiments, the processor may determine the test parameters by looking up a parameter table based on the soil slope structure data. The parameter table may be preset based on manual experience. The parameter table may include recommended test parameters under different soil slope structure data. For example, the table may record [sand, inclination 10°, thickness 30 cm] and recommend [rainfall pattern B, rainfall intensity 1500 ml/min, rainfall amount 10 L].

The processor may determine the appropriate test parameters such that more valid data can be obtained during a time process and waste of resources can be avoided.

In some embodiments, the rainfall simulation unit may further include a precipitation regulation valve 25 and a slide rail mechanism capable of moving along slide rails. The precipitation regulation valve 25 may be connected with the flexible pipes 72 and the rigid pipe 71, respectively. In some embodiments, the precipitation regulation valve 25 may be any one of a one-to-four water valve, an electromagnetic proportional valve, and a precision regulation valve.

In some embodiments, the slide rail mechanism may be composed of at least two parallel rails. The at least two parallel rails may be made of metal bars or other solid materials. A platform capable of sliding along the slide rails may be mounted on the slide rails, and the plurality of spray nozzles 6 may be disposed on the platform, thereby realizing multi-directional precipitation simulation.

In some embodiments, the processor may be configured to: generate a rainfall instruction and a sliding instruction based on the test parameters; send the rainfall instruction to the precipitation regulation valve 25 and the water pump 9, and send the sliding instruction to the slide rail mechanism. The rainfall instruction refers to an instruction for controlling parameters such as the rainfall pattern, the rainfall intensity, and the rainfall amount. The sliding instruction refers to an instruction for controlling the slide rail mechanism to drive the plurality of spray nozzles 6 to move to control rainfall positions.

In some embodiments, the test parameters may be obtained by looking up the table as described above to obtain the recommended test parameters, or may be configured by test personnel according to actual needs.

With the combination of the slide rails and the precipitation regulation valve 25, various rainfall patterns and intensities can be simulated, thereby increasing the diversity and accuracy of the simulation, and obtaining more abundant test data.

Figure 2:
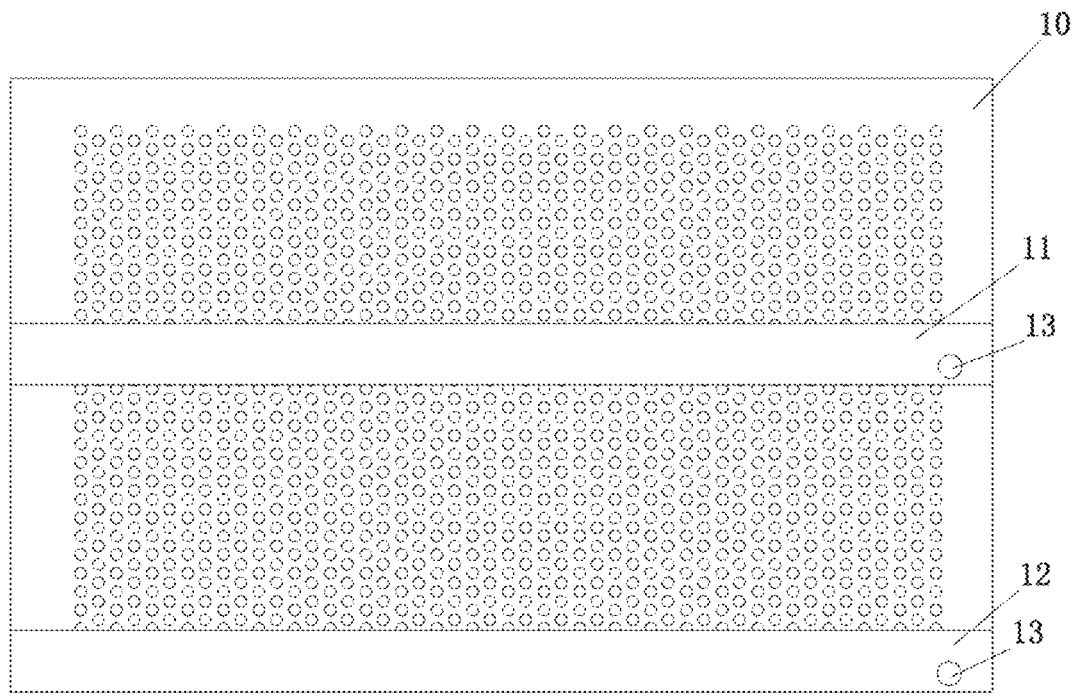
FIG. 2 a schematic structural diagram illustrating an exemplary porous plate at a first viewing angle according to some embodiments of the present disclosure.
Figure 3:
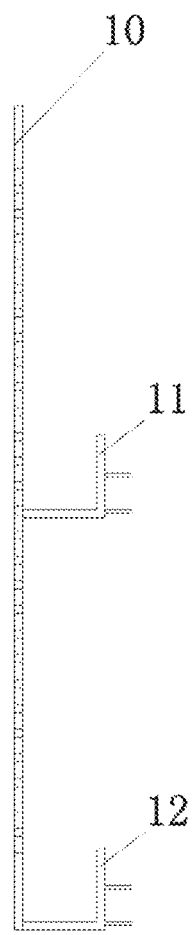
FIG. 3 a schematic structural diagram illustrating an exemplary porous plate at a second viewing angle according to some embodiments of the present disclosure.

Referring to FIGS. 2-3, FIGS. 2-3 are schematic structural diagrams illustrating an exemplary porous plate at a first viewing angle and a second viewing angle. In some embodiments, a runoff-seepage separation unit may include the porous plate 10 disposed at an end of the model slot 2. The runoff water chute 11 may be disposed at a position behind the porous plate 10 corresponding an upper portion of the soil slope 1. The seepage water chute 12 may be disposed at a position behind the porous plate 10 corresponding a bedrock surface of the soil slope 1.

In some embodiments, the runoff water chute 11 and the seepage water chute 12 may be coordinated with a monitoring module through a first guide pipe 13, respectively.

In some embodiments, a position of the runoff water chute 11 may correspond to a filling height of the slope and configured to collect surface runoff generated by rainfall acting on the slope 1. The seepage water chute 12 may be disposed at a lower portion of the porous plate 10 and configured to collect seepage water passing through the porous plate 10 within the slope under the effect of rainfall. The two first guide pipes 13 may be disposed at a water outlet of the runoff water chute 11 and the seepage water chute 12, respectively, and configured to guide the runoff and the seepage of the slope 1.

Referring to FIG. 1, in some embodiments, the monitoring module may further include a plurality of sensors disposed inside the soil slope 1 and configured to monitor changes in water content and pore water pressure within the slope under the effect of rainfall; and one or more cameras 14 disposed at a side of the soil slope simulation unit and configured to record a morphological change of the soil slope 1.

In some embodiments, the flow rate monitoring unit may include two sedimentation tanks 15 connected with the runoff water chute 11 and the seepage water chute 12, respectively. Each of the two sedimentation tanks 15 may be connected with the corresponding water collection tank 17 through the corresponding second guide pipe 16. The weighing device 18 may be provided under each of the two sedimentation tanks 15 and the water collection tank 17.

In some embodiments, the second guide pipe 16 may be disposed at an upper edge of the corresponding sedimentation tank 15. A horizontal height of the water collection tank 17 may be lower than a horizontal height of the corresponding sedimentation tank 15.

In some embodiments, the plurality of sensors may include a plurality of pore water pressure sensors 19 and a plurality of water content sensors 20 for collecting changes in parameters within the soil slope 1 under the effect of rainfall. The plurality of pore water pressure sensors 19 and the plurality of water content sensors 20 may be buried at different depths within the soil slope 1 along a direction perpendicular to the bedrock surface.

In some embodiments, each of the two sedimentation tanks 15 may be a silt sedimentation tank which is a lidless cuboid plastic tank with an overflow port and placed near the water outlet of the corresponding runoff water chute 11 and the seepage water chute 12, respectively. During the test process, the silt sedimentation tank may always keep full of water, drainage of the runoff water chute 11 and the seepage water chute 12 may be drained into the small particle (smaller than a mesh aperture) sedimentation tank 15 through the corresponding first guide pipe 13, and silt brought out by the water flow may be deposited at a bottom of the sedimentation tank 15 under the action of the weight.

In some embodiments, the water flowing through the two sedimentation tanks 15 may overflow through the overflow port and may be drained into the corresponding water collection tank 17 through the corresponding second guide pipe 16 to achieve the purpose of water and soil separation. During the implementation process, the water collecting tank 17 may be provided with a drainage valve 23 to control the drainage of the water collection tank 17.

In some embodiments, the weighing device 18 may be configured to monitor the mass changes of the water collection tank 17 and the water supply end 8 in real time, thereby realizing automatic real-time monitoring of the runoff and seepage flow rates and the rainfall intensity.

In some embodiments, the plurality of pore water pressure sensors 19 and the plurality of water content sensors 20 may be buried at different depths within the soil slope 1 along the direction perpendicular to the bedrock surface to collect soil slope parameters. In actual application, the soil slope parameters may include but are not limited to the parameters within the soil slope such as the pore water pressure and the soil water content, which can be further extended by those skilled in the art.

In some embodiments, one or more cameras 14 may include two cameras 14 which are disposed at one of left and right sides and a front side of a model tank of the soil slope simulation unit, respectively.

In some embodiments, the processor may be configured to: obtain a runoff data sequence, a seepage data sequence, a sedimentation weight sequence, and a water supply tank weight sequence based on the monitoring module; determine a soil loss weight sequence based on the sedimentation weight sequence and the water supply tank weight sequence; and determine camera parameters of the plurality of cameras 14 based on the runoff data sequence, the seepage data sequence, and the soil loss weight sequence.

In some embodiments, the runoff data sequence, the seepage data sequence, the sedimentation weight sequence, and the water supply tank weight sequence may all be sequences obtained in a chronological order. Taking the sedimentation weight sequence as an example, elements of the sedimentation weight sequence may correspond to total weights of water and soil loss in the two sedimentation tanks 15 at different time, respectively.

In some embodiments, the soil loss weight sequence may be determined by calculation based on the sedimentation weight sequence and the water supply tank weight sequence. Taking the runoff as an example, assuming that a weight of runoff soil entering the two sedimentation tanks 15 is $x_1$, and a weight of water entering the two sedimentation tanks 15 is $x_2$; after the water and the soil loss enter the two sedimentation tanks 15, a corresponding volume of water in the two sedimentation tanks 15 may be squeezed into the water collection tank 17, and at this time, a volume of this part of water may also be obtained according to the weight of the water collection tank 17.

Then:

$$\frac{x_1}{\rho_1} + \frac{x_2}{\rho_2} = L \text{ and } x_1 + x_2 + (m_1 - L * \rho_2) = m_2$$

may be obtained, wherein $\rho_1$ denotes density of soil loss, $\rho_2$ denotes density of water, L denotes the volume (i.e. the volume of soil loss+the volume of water entering the two sedimentation tanks 15) of water squeezed into the water collection tank 17, $m_1$ denotes original weights of the two sedimentation tanks 15, and $m_2$ denotes weights of the two sedimentation tanks 15 after the runoff soil loss and the water flow into the two sedimentation tanks 15. Since the density of the soil loss, the density of water, the volume of water squeezed into the water collection tank 17, the original weights of the two sedimentation tanks 15, and the weights of the two sedimentation tanks 15 after the water flows into the two sedimentation tanks 15 can be directly obtained, the weight $x_1$ of the runoff soil entering the two sedimentation tanks 15 and the weight $x_2$ of the water entering the two sedimentation tanks 15 may be obtained by calculation. Similarly, the weight of seepage soil may be obtained by calculation, and then the soil loss weight sequence may be determined.

The one or more cameras 14 may be configured to record the morphological change of the slope. When the morphological change of the slope is not large, if sampling frequencies of the one or more cameras 14 are set to a high level, most of images captured by the one or more cameras 14 may be repeated and constant images, resulting in an increase in test cost. When the morphological change of the slope is large, if the sampling frequencies of the one or more cameras 14 are set to a low level, image information obtained by the one or more cameras 14 may be insufficient to reflect an actual morphological change of the slope. Therefore, in some embodiments, the processor may determine the camera parameters of the one or more cameras 14 based on the runoff data sequence, the seepage data sequence, and the soil loss weight sequence. The camera parameters may be the sampling frequencies (i.e., the frequencies of the one or more cameras 14 taking pictures) or resolutions of the one or more cameras 14.

In some embodiments, the processor may increase the camera parameters when a total soil loss weight and/or a soil loss rate is greater than a preset threshold. The greater the soil loss weight and/or the soil loss rate, the greater the adjustment range of the camera parameters. The soil loss rate may be obtained by calculating (e.g. a slope value) two adjacent elements in the soil loss weight sequence. Adjustment values of the camera parameters may be determined according to the actual parameters, which are not limited in the present disclosure.

In some embodiments, since factors causing the landslide are related to the runoff and the seepage, the processor may construct landslide feature vectors at a plurality of time points based on the soil loss weight sequence, the runoff data sequence, and the seepage data sequence. The constructed landslide feature vector at a single time point may include three dimensions. For example, assuming that at time t, the soil loss weight may be X', the runoff data may be Y', and the seepage data may be Z' based on the soil loss weight sequence, the runoff data sequence, and the seepage data sequence, the constructed landslide feature vector at time t may be (X', Y', Z').

In some embodiments, the processor may determine the camera parameters by performing vector matching in a vector database based on the landslide feature vectors. The vector database may be preset based on artificial experience. The vector database may include a plurality of reference vectors and corresponding camera parameters determined based on experience. In some embodiments, the processor may calculate vector distances (e.g., a Manhattan distance or a cosine distance, etc.) between the landslide feature vectors and the plurality of reference vectors, use reference vectors with the shortest vector distance as target vectors, and use camera parameters corresponding to the target vectors as the camera parameters of the landslide feature vectors. It should be noted that other conventional algorithms may also be used for vector matching, which are not limited in the present disclosure.

The test analysis efficiency may be improved through real-time control of the camera parameters, and the increase in the test cost caused by repeated shooting may be reduced.

In some embodiments, the monitoring module may further include a plurality of sedimentation cameras configured to capture sedimentation images of the two sedimentation tanks 15 at a plurality of angles at the same time point to obtain a plurality of sedimentation images corresponding to the plurality of time points.

In some embodiments, the processor may be further configured to determine the soil loss weight sequence through a soil loss weight determination model based on the slope soil quality data, the sedimentation weight sequence, the water supply tank weight sequence, the soil slope image sequence, and the sedimentation image sequence.

In some embodiments, the soil loss weight determination model may be a machine learning model. For example, the soil loss weight determination model may be a trained convolutional neural networks (CNN) model. An input of the soil loss weight determination model may include the slope soil quality data, the sedimentation weight sequence, the water supply tank weight sequence, the soil slope image sequence, and the sedimentation image sequence, and an output of the soil loss weight determination model may include the soil loss weight sequence. The soil slope image sequence and the sedimentation image sequence may be a collection of images at the plurality of time points. Each of the plurality of time points may correspond to a plurality of images of the soil slope or the two sedimentation tanks 15 at a plurality of angles.

The model may be obtained by training based on training samples. In some embodiments, a plurality of training samples with labels may be input into an initial soil loss weight determination model. A loss function may be constructed through the labels and results of the soil loss weight determination model. Parameters of an initial environmental assessment model may be iteratively updated by gradient descent or other methods based on the loss function. When a preset condition is met, the model training may be completed, and a trained soil loss weight determination model may be obtained. The preset conditions may be that the loss function converges, a count of iterations reaches a threshold, etc. In some embodiments, the training samples may include sample slope soil quality data, sample sedimentation weight sequence, sample water supply tank weight sequence, sample soil slope image sequence, and sample sedimentation image sequence, and the labels may include real soil loss weight sequences corresponding to the samples. The training sample may be obtained based on historical experiments. The labels may be obtained by manually weighing the soil loss obtained after the water in the two sedimentation tanks 15 are drained in case of the corresponding samples, or by computer simulation (e.g., finite element analysis).

By acquiring the sedimentation images and using the soil loss weight determination model, the problem of inaccurate calculation result of the soil loss weight caused by uneven density of the soil loss or soil adsorption on a pipe wall may be effectively avoided.

In some embodiments, the processor may be further configured to determine a soil slope deformation degree sequence based on the soil slope image sequence; and determine the camera parameters based on the soil slope deformation degree sequence.

The soil slope image sequence may include a collection of soil slope images obtained in a current test before the processor performs the operation. In some embodiments, the processor may obtain initial edge shape data corresponding to an initial soil slope based on a most initial image of the soil slope in the soil slope image. Then, the processor may obtain edge shape data corresponding to other soil slope images in the soil slope image sequence, and determine a difference between the other edge shape data and the initial edge shape data, thereby obtaining the soil slope deformation degree sequence.

Elements of the soil slope deformation degree sequence may include difference degrees between edge shape data corresponding to soil slope images taken at different times and the initial edge shape data. In some embodiments, the difference degree may be a value between 0 and 1. In the soil slope deformation degree sequence, the greater the difference between the other edge shape data and the initial edge shape data, the greater the corresponding element value. The edge shape data may be obtained by processing the images using algorithms such as Canny edge detection, a Sobel operator, a Laplacian operator, etc.

In some embodiments, if values of one or more elements in the soil slope deformation degree sequence are greater than a threshold, the camera parameters may be increased; and the greater the values of the elements greater than the threshold, the greater the adjustment values of the increased camera parameters. In some embodiments, if a mean value of the elements in the soil slope deformation degree sequence is greater than a preset threshold, the adjustment values of the camera parameter may also be increased accordingly. The adjustment values of the camera parameters may be determined according to actual parameters (e.g., the sampling frequencies or the solutions), which are not limited in the present disclosure.

By analyzing the soil slope images, the camera parameters may be adjusted in time to increase access to valid test information.

The present disclosure further provides a test method of a landslide model test device for realizing multi-variable synchronous monitoring. The method may include: piling up a soil slope model and simulating different inclinations of the slope by a soil slope simulation unit, simulating rainfall of different intensities and inducing a landslide by a rainfall simulation unit, implementing separation of runoff from seepage at the soil slope simulation unit by a runoff-seepage separation unit during simulation of rainfall of different intensities, and monitoring runoff and seepage flow rates of the slope, changes in water content and pore water pressure within the slope, and a morphological change of the slope under the effect of rainfall by a monitoring module, to obtain a mechanism of rainfall-induced landslide deformation and damage based on synergistic analysis of multi-variable data.

In some embodiments, the runoff and the seepage may be firstly separated. After separation, the seepage and the runoff may enter respective water collection tanks 17. An electronic scale may be disposed at a bottom of the water collection tank 17 to read gravity data in real time. A real-time change in the gravity data may be a real-time dynamic change in the runoff and seepage flow rates, i.e., the faster the gravity change, the greater the flow rate, and then the real-time flow rate may be quantified. In order to ensure continuous monitoring, two parallel seepage and runoff water collection and weight measurement devices may be provided for alternate water collection to achieve continuous operation of monitoring. With application of the device, the flow rate changes in the seepage and the runoff can be obtained without relying on manual real-time monitoring.

The landslide model test device and method for realizing multi-variable synchronous monitoring provided in some embodiments of the present disclosure have but not limited to the following beneficial effects.

(1) With the runoff-seepage separation unit in the landslide model, the surface runoff and the seepage within the slope under the effect of rainfall can be effectively separated, and the related data can be collected for analysis.

(2) The runoff and seepage flow rates can be automatically monitored in real time using the monitoring module. Meanwhile, the changes in the parameters of the soil slope, including but not limited to the pore water pressure and the soil water content, and the morphological change of slope can be monitored in real time, thereby obtaining multi-angle data on the slope response to the rainfall.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure and are within the spirit and scope of the exemplary embodiments of the present disclosure.

Moreover, certain terminology has been used to describe embodiments of the present disclosure. For example, the terms "one embodiment," "an embodiment," and "some embodiments" mean that a particular feature, structure, or feature described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or features may be combined as suitable in one or more embodiments of the present disclosure.

In addition, unless explicitly stated in the claims, the order of the processing elements and sequences described, the use of alphanumeric characters, or the use of other names in the present disclosure are not intended to limit the order of the processes and methods of the present disclosure. Although the above disclosure discusses some invention embodiments that are currently considered useful through various examples, it should be understood that such details are only for illustrative purposes, and the attached claims are not limited to the disclosed embodiments. On the contrary, the claims are intended to cover all modifications and equivalent combinations that are consistent with the essence and scope of the embodiments of the present disclosure.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

Finally, it should be understood that the embodiments described in the present disclosure are only used to illustrate the principles of the embodiments of the present disclosure. Other variations may also fall within the scope of the present disclosure. Therefore, as an example and not a limitation, alternative configurations of the embodiments of the present disclosure may be regarded as consistent with the teaching of the present disclosure. Accordingly, the embodiments of the present disclosure are not limited to the embodiments introduced and described in the present disclosure explicitly.

What is claimed is:

1. A landslide model test device for realizing multi-variable synchronous monitoring, comprising:
   a soil slope simulation unit, configured to pile up a soil slope and simulate different inclinations of the slope, the soil slope simulation unit including a model slot;
   a rainfall simulation unit, cooperated with the soil slope simulation unit and configured to simulate rainfall of different intensities and induce a landslide;
   a runoff-seepage separation unit, disposed at an end of the soil slope simulation unit and configured to implement separation of runoff from seepage of the slope under the effect of rainfall; the runoff-seepage separation unit including a porous plate disposed at an end of the model slot, wherein a runoff water chute is disposed at a position behind the porous plate corresponding a slope surface of the soil slope, and a seepage water chute is disposed at a position behind the porous plate corresponding a bedrock surface of the soil slope; and
   a monitoring module, cooperated with the runoff-seepage separation unit and configured to monitor runoff and seepage flow rates of the slope, changes in water content and pore water pressure within the slope, and a morphological change of the slope under the effect of rainfall; wherein the monitoring module includes a flow rate monitoring unit, disposed at an end of the runoff-seepage separation unit and configured to monitor the runoff and seepage flow rates of the slope under the effect of rainfall; wherein the flow rate monitoring unit includes two sedimentation tanks connected with the runoff water chute and the seepage water chute, respectively, each of the two sedimentation tanks is connected with a water collection tank through a second guide pipe; the second guide pipe is disposed at an upper edge of the corresponding sedimentation tank; a horizontal height of the water collection tank is lower than a horizontal height of the corresponding sedimentation tank; and a weighing device is provided under each of the two sedimentation tanks and the water collection tank.

2. The landslide model test device of claim 1, wherein the soil slope is disposed in the model slot; a hoisting mechanism is disposed at a front end of the model slot in a cooperated manner, a bottom of a rear end of the model slot is hinged on a hinge support, and the hinge support is placed on a horizontal plane.

3. The landslide model test device of claim 2, wherein the hoisting mechanism includes a bracket disposed on the horizontal plane, a chain hoist is disposed at an upper portion of the bracket, and the chain hoist is cooperated with a hanging ring disposed at the front end of the model slot through a hoisting ring.

4. The landslide model test device of claim 2, wherein the rainfall simulation unit includes one or more spray nozzles cooperated with an upper portion of the model slot, the one or more spray nozzles being connected with a water supply end through a water inlet pipe.

5. The landslide model test device of claim 2, wherein the runoff water chute and the seepage water chute are cooperated with the monitoring module through a first guide pipe.

6. The landslide model test device of claim 1, wherein the monitoring module further includes:
   a plurality of sensors, disposed within the soil slope and configured to monitor the changes in the water content and the pore water pressure within the soil slope under effect of rainfall; and
   one or more cameras, disposed at a side of the soil slope simulation unit and configured to record the morphological change of the soil slope.

7. The landslide model test device of claim 6, wherein the plurality of sensors include a plurality of pore water pressure sensors and a plurality of water content sensors configured to collect changes in parameters within the soil slope under the effect of rainfall; the plurality of pore water pressure sensors and the plurality of water content sensors being buried at different depths within the soil slope in a direction perpendicular to the bedrock surface.

8. A landslide model test method, implemented by the landslide model test device for realizing multi-variable synchronous monitoring of claim 1, comprising:
   piling up a soil slope and simulating different inclinations of the slope by a soil slope simulation unit,
   simulating rainfall of different intensities and inducing a landslide by a rainfall simulation unit;
   implementing separation of runoff from seepage at the soil slope simulation unit by a runoff-seepage separation unit during simulation of rainfall of different intensities, and monitoring runoff and seepage flow rates of the slope, changes in water content and pore water pressure within the slope, and a morphological change of the slope under the effect of rainfall by a monitoring module, to obtain a mechanism of rainfall-induced landslide deformation and damage based on synergistic analysis of multi-variable data.

* * * * *